(12) United States Patent
Hummen et al.

(10) Patent No.: US 9,925,077 B2
(45) Date of Patent: Mar. 27, 2018

(54) STENT APPLICATOR

(71) Applicant: Carag AG, Baar (CH)

(72) Inventors: Jörg Hummen, Merlischachen (CH); Kuno Limacher, Steinhausen (CH); Cyrill Röthlin, Hünenberg (CH); Claudio Steiner, Baar (CH); Beat Widmer, Lucerne (CH); Albora De Pablo Peña, Zürich (CH); Jérôme Bernhard, Zürich (CH); Christoph Sidler, Ebikon (CH)

(73) Assignee: CARAG AG, Baar (CH)

( * ) Notice: Subject to any disclaimer, the term of this patent is extended or adjusted under 35 U.S.C. 154(b) by 344 days.

(21) Appl. No.: 14/651,412

(22) PCT Filed: Dec. 5, 2013

(86) PCT No.: PCT/CH2013/000215
§ 371 (c)(1),
(2) Date: Jun. 11, 2015

(87) PCT Pub. No.: WO2014/089715
PCT Pub. Date: Jun. 19, 2014

(65) Prior Publication Data
US 2015/0313739 A1 Nov. 5, 2015

(30) Foreign Application Priority Data
Dec. 11, 2012 (CH) ........................................ 2771/12

(51) Int. Cl.
*A61F 2/966* (2013.01)
*A61F 2/95* (2013.01)
*A61F 2/962* (2013.01)

(52) U.S. Cl.
CPC .............. *A61F 2/966* (2013.01); *A61F 2/962* (2013.01); *A61F 2002/9505* (2013.01); *A61F 2002/9517* (2013.01); *A61F 2002/9534* (2013.01)

(58) Field of Classification Search
CPC .. A61F 2/95; A61F 2/962; A61F 2/966; A61F 2002/9505; A61F 2002/9534
See application file for complete search history.

(56) References Cited

U.S. PATENT DOCUMENTS

| 7,001,423 | B2* | 2/2006 | Euteneuer | A61F 2/95 606/198 |
| 7,163,552 | B2* | 1/2007 | Diaz | A61F 2/95 623/1.12 |
| 9,271,855 | B2* | 3/2016 | Green | A61F 2/966 |
| 2005/0288764 | A1* | 12/2005 | Snow | A61F 2/95 623/1.11 |
| 2006/0030923 | A1 | 2/2006 | Gunderson | |
| 2006/0184226 | A1 | 8/2006 | Austin | |
| 2008/0132989 | A1 | 6/2008 | Snow et al. | |

(Continued)

FOREIGN PATENT DOCUMENTS

EP 1 208 816 A2 5/2002
WO 00/18330 A1 4/2000

(Continued)

OTHER PUBLICATIONS

International Preliminary Search Report for International PCT Application No. PCT/CH2013/000215, dated Jun. 25, 2015.

*Primary Examiner* — Diane Yabut
(74) *Attorney, Agent, or Firm* — McDonnell Boehnen Hulbert & Berghoff LLP

(57) ABSTRACT

The invention relates to a delivery system for delivering a stent (S) into a body vessel of a patient, comprising a flexible catheter tube (3) having a proximal and a distal end for (Continued)

delivering the stent (S) to a predetermined location in the body vessel and a catheter tip (1) having a longitudinal direction, which is disposed at the distal end of the catheter tube (3). The catheter tip (1) has a stent chamber (150) to receive the stent (1). The catheter tip has a first pressure chamber (20, 22). In the catheter tube (3) a first fluid channel (31) extends from the proximal end to the first pressure chamber (20, 22) of the catheter tip (1). The volume of the first pressure chamber (20, 22) can be enlarged by delivering a first fluid from the first fluid channel (31) to the first pressure chamber (20, 22), such that the stent (S) is released from the stent chamber (150) at the predetermined location in the body vessel. According to the invention the catheter tip (1) has a second pressure chamber (21, 23), wherein in the catheter tube (3) a second fluid channel (32) extends from the proximal end to the second pressure chamber (21, 23) and wherein the volume of the second pressure chamber (21, 23) can be enlarged by delivering a second fluid from the second fluid channel (32) to the second pressure chamber (21, 23), such that a partially released stent (S) can be returned from the predetermined location in the body vessel into the stent chamber (150). This delivery system according to the invention makes it possible to release a stent (S) at a well-defined location and also to surround same again relatively atraumatically and to reposition same in situ.

16 Claims, 7 Drawing Sheets

(56) References Cited

U.S. PATENT DOCUMENTS

2009/0024137 A1\* 1/2009 Chuter ..................... A61F 2/95
                                                        606/108
2011/0276121 A1   11/2011 Levine

FOREIGN PATENT DOCUMENTS

| WO | 08/008642 A1 | 1/2008 |
| WO | 09/011866 A1 | 1/2009 |
| WO | 10/130443 A1 | 11/2010 |

\* cited by examiner

STENT APPLICATOR

TECHNICAL FIELD

This application is a US national phase of International Application No. PCT/CH2013/000215 filed on Dec. 5, 2013, which claims priority to Switzerland Patent Application No. 2771/12 filed on Dec. 11, 2012.

The present invention relates to a stent applicator, i.e. a delivery system for guiding a stent in a body of a patient in accordance with the preamble of patent claim 1, and to a catheter head.

PRIOR ART

Stents and applicators for inserting and unfolding stents are known with many different embodiments in the prior art. A stent is usually a cylindrical prosthesis, which is introduced into a vessel or a lumen of a patient and radially expanded there. Stents are employed in very different regions, for example as heart valve stents, coronary stents or peripheral stents. In preferred embodiments, the stents have a self-expanding embodiment, particularly by means of a spring force. For example balloon-expanded stents are also known.

Catheters with a specifically embodied catheter tip are usually used as a delivery system, which is also referred to as a stent applicator. This tip surrounds the compressed stent and it is embodied in such a way that, as stipulated by the medical practitioner, it can release the stent at the desired position. It is necessary for this catheter, and in particular this tip, to have an external diameter which is as small as possible.

Stent applicators which have a mechanism with pull and push rods are very widespread.

However, the prior art has also disclosed stent applicators which are actuated by a fluid in order to release the stent. Examples for this include EP 0 746 375, EP 1 565 227, WO 2005/115524, EP 0 705 578, WO 2008/153765, U.S. Pat. No. 6,113,608, EP 1 208 816, U.S. Pat. No. 6,056,759, U.S. Pat. No. 6,027,474 and WO 2006/096229.

Furthermore, WO 2009/011866 discloses a delivery system for stents with a double-acting cylinder arranged in the manipulation instruments of the catheter. This system is intended to simplify the unfolding of the stent.

These stent applicators enable a release of a stent at the desired point within a body vessel. However, they are unsuitable for re-sheathing a partly or wholly released stent, repositioning it or completely removing it from the body again.

However, such repositioning or removal of the stent is often desired. By way of example, the stent may be dislocated during the implantation on the beating heart, and so it once again has to be positioned anew.

SUMMARY OF THE INVENTION

It is therefore an object of the invention to develop a delivery system for a stent which enables not only releasing, but also a re-sheathing of the stent.

This object is achieved by a delivery system having the features of patent claim 1.

The delivery system according to the invention for delivering a stent in a body of a patient, for example in a vessel or a lumen, comprises a flexible catheter tube with a proximal and a distal end for delivering the stent to a predetermined point in the body vessel and a catheter tip with a longitudinal direction, which is arranged at the distal end of the catheter tube. The catheter tip has a stent chamber for receiving the stent. The catheter tip has a first pressure chamber. A first fluid channel extends in the catheter tube from the proximal end to the first pressure chamber of the catheter tip. A volume of the first pressure chamber is enlargeable by delivering a first fluid from the first fluid channel to the first pressure chamber, wherein, as a result thereof, the stent is releasable from the stent chamber at the predetermined point in the body vessel. According to the invention, the catheter tip has a second pressure chamber. A second fluid channel extends in the catheter tube from the proximal end to the second pressure chamber. A volume of the second pressure chamber is enlargeable by delivering a second fluid from the second fluid channel to the second pressure chamber, as a result of which a partly released stent is retractable into the stent chamber from the predetermined point in the body vessel.

In this text, "proximal" and "back" mean facing the medical practitioner and facing away from the patient. In this text, "distal" and "front" mean facing away from the medical practitioner and facing the patient.

The stent applicator according to the invention enables not only precise positioning of a stent in a vessel of a patient, but also the retraction thereof in situ. It is only possible to retract the stent under all circumstances in the partly released stage. Retracting and re-sheathing a completely released stent is dependent on the shape and type of the stent and the connection thereof to the stent applicator, but it is also possible using the mechanism according to the invention.

Thanks to the system according to the invention, the stent can be positioned precisely at the position at which it already lay in a sheathed condition. Unlike what is conventional in the prior art, it is not displaced forward. Rather, the sheath thereof is pulled away to the back. This enables precise positioning of the stent within the body opening or the body channel.

In preferred embodiments, the delivery system has a double-action hydraulic cylinder, which releases and re-sheaths the stent. Preferably, the two pressure chambers in the catheter tip are not connected to one another, i.e. they do not exchange fluids. Preferably, the whole system does not interchange the two fluids.

The catheter tube is preferably embodied as a multi-lumen catheter tube which has at least two lines separate from one another and preferably one lumen for a guide wire. This tube at the same time serves as a flexible plunger rod for displacing the at least one catheter plunger arranged in the catheter tip or said tube acts as a plunger itself.

In preferred embodiments, the catheter tube no longer moves during the release and re-sheathing of the stent after it has brought the catheter tip to the predetermined point in the body vessel. In other embodiments, only an inner part of the catheter tube remains immobile and an outer part moves during the release and/or during the re-sheathing of the stent.

In preferred embodiments, the catheter tip has a first sleeve, in which one of the first and second pressure chamber is arranged, and a second sleeve, in which the other one of the first and second pressure chamber is arranged.

Preferably, the catheter tube has a guide lumen for passing a guide wire therethrough, wherein the first sleeve and the second sleeve are displaceable relative to this guide lumen and wherein the guide lumen remains unchanged in terms of its location in respect of the predetermined point and the first and second sleeve move relative to the predetermined point.

In a preferred embodiment, the first sleeve and the second sleeve are arranged in succession in the longitudinal direction, wherein, in the longitudinal direction, they are connected to one another in a non-displaceable manner relative to one another.

Preferably, the first sleeve and the second sleeve are displaceable together relative to the catheter tube in the longitudinal direction.

So that the catheter tip can also be pushed around tight bends without traumatizing the surrounding tissue when it is pushed through body channels, the catheter tip preferably has at least one flexible region such that it is flexible transverse to the longitudinal direction. This renders it possible to embody the catheter tip in a relatively long manner and, in particular, arrange the two pressure chambers in succession.

In a preferred embodiment, a first catheter plunger which forms a distal end of the first pressure chamber is arranged at the distal end of the catheter tube, wherein the first sleeve is displaceable in the longitudinal direction in a sealing sliding manner relative to this first catheter plunger, wherein the first pressure chamber has a first sleeve base which forms a proximal end of the first pressure chamber, wherein the first sleeve base is securely connected to the first sleeve and arranged in a sealing sliding manner around the catheter tube, wherein a second catheter plunger which forms a proximal end of the second pressure chamber is arranged on the catheter tube, wherein the second sleeve is displaceable in the longitudinal direction in a sealing sliding manner relative to this second catheter plunger, wherein the second pressure chamber has a second sleeve base which forms a distal end of the second pressure chamber, and wherein the second sleeve base is securely connected to the second sleeve and arranged in a sealing sliding manner around the catheter tube.

This embodiment can be embodied with a very narrow diameter.

In another preferred embodiment, the second sleeve is arranged within the first sleeve and in a manner displaceable relative to the latter. Preferably, the catheter tube in this embodiment has an outer tube portion and an inner tube portion arranged therein, wherein the outer tube portion is displaceable in the longitudinal direction relative to the inner tube portion, wherein the first sleeve is securely connected to the outer tube portion and displaceable in the longitudinal direction in a sealing sliding manner in relation to the inner tube portion, wherein a catheter plunger is present, which plunger is securely connected to the inner tube portion and displaceable in the longitudinal direction in a sealing manner relative to the inner sleeve, wherein the second sleeve is sealed at the proximal end thereof by a sleeve base, which is securely connected to the former and which is displaceable in the longitudinal direction in a sealing sliding manner relative to the first sleeve, wherein the first pressure chamber is embodied between the sleeve base and the catheter plunger, and the second pressure chamber is embodied between a proximal end of the first sleeve and the sleeve base. This embodiment has a relatively short length.

In both and further embodiments, the catheter plunger closest to the distal end of the catheter tube preferably forms a distal end of the stent chamber. That is to say the stent chamber is arranged in front of the two pressure chambers.

In both and further embodiments, the catheter tip, at the distal end thereof, has a catheter head in the form of spring leaves, wherein the spring leaves are inclined with respect to one another in a petaloid or bud-shaped manner and at least partly close an opening to the stent chamber. Preferably, each spring leaf has an inwardly directed protrusion. It is also possible to use other shapes of atraumatic catheter heads.

The delivery system preferably has a manipulation part which is arranged at the proximal end of the catheter tube, wherein, by means of the manipulation part, the stent can be released from, and returned back into, the stent chamber at the predetermined point in the body vessel.

In a preferred embodiment, the manipulation part has a hydraulic apparatus with a first fluid chamber with a first plunger and a second fluid chamber with a second plunger, wherein a proximal end of the first fluid lumen is connected to the first fluid chamber and a proximal end of the second fluid lumen is connected to the second fluid chamber. Here, preferably, the first plunger is actuatable by means of an actuation lever and the second plunger is actuatable by means of a rotary knob.

It is a further object of the invention to develop a catheter head which is as atraumatic as possible.

This object is achieved by a catheter head having the features of claim 17.

The catheter head according to the invention has spring leaves which are inclined with respect to one another in a petaloid or bud-shaped manner and which open from the inside to the outside by pressure.

Preferably, the spring leaves automatically spring back into the bud shape thereof after releasing a stent.

In order to simplify the release of a stent and also, where applicable, a re-sheathing, the spring leaves preferably have inwardly directed protrusions.

The risk of traumatization can be further reduced if the spring leaves are together surrounded by a flexible protection tube which extends outwardly when the spring leaves are opened and which is elastic enough to rest against the spring leaves again when these are closed again.

This catheter head is suitable for various applications, but in particular for use in a delivery system as described in this text.

Further embodiments are specified in the dependent claims.

BRIEF DESCRIPTION OF THE DRAWINGS

Preferred embodiments of the invention are described below on the basis of the drawings, which merely serve for explanatory purposes and are not intended to be interpreted as being restrictive. In the drawings.

DESCRIPTION OF PREFERRED EMBODIMENTS

Figure 1:
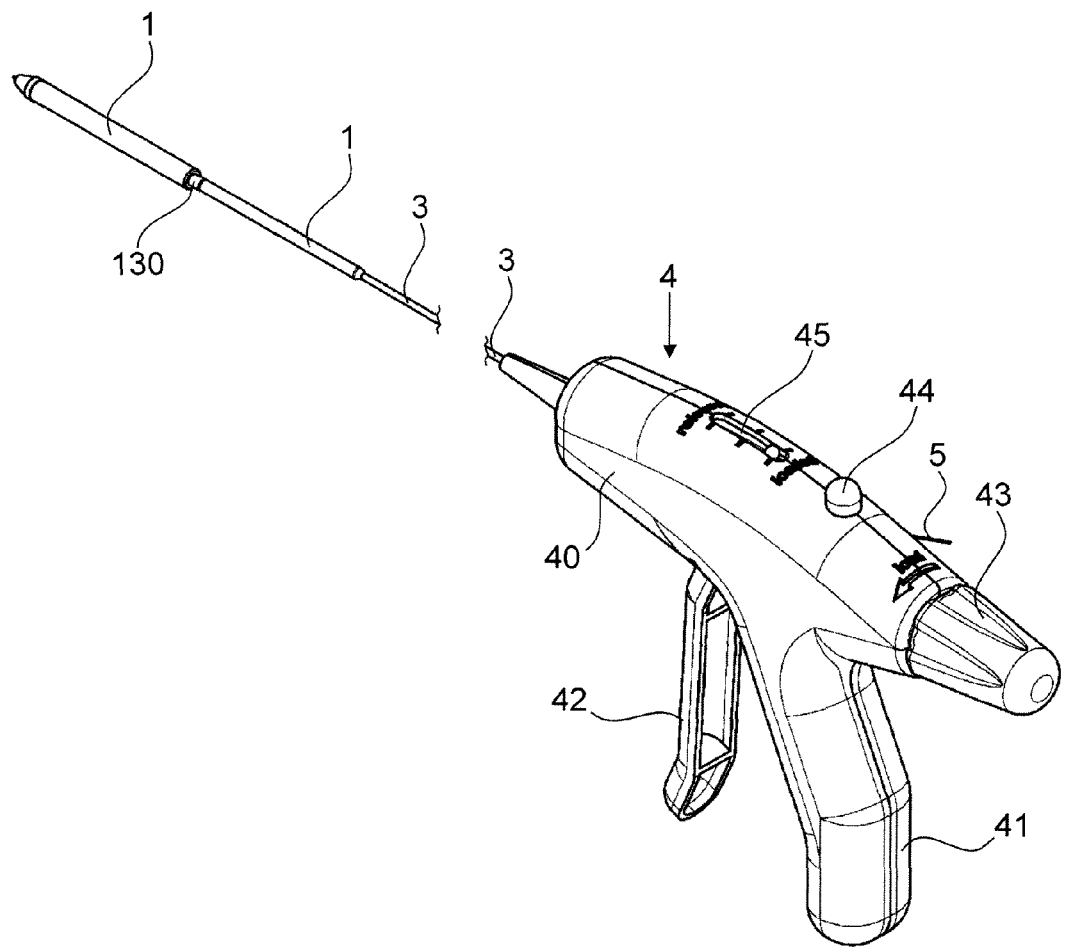
FIG. 1 shows a perspective illustration of a stent applicator according to the invention in a first embodiment.

FIGS. 1 to 6 depict a first exemplary embodiment of a stent applicator according to the invention. It has a manipulation instrument in the form of a pistol-shaped, rigid handheld part 4. This handheld part 4 has a main body 40 with, formed thereon, a handle 41 for holding the instrument in the hand of the medical practitioner or user. An actuation lever 42 can be pulled towards the handle 41 by the fingers of the hand which holds the handle 41.

A flexible catheter tube 3 is fastened to the handheld part 4. Preferably, it is detachably connected thereto. However, it can also be connected securely or in a manner not detachable in a nondestructive manner to the handheld part 4. The catheter tube 3 is manufactured from a flexible material, in particular Pebax. It has a length matched to the field of application of the stent applicator. In the figures, it is depicted with an interruption in its length.

At the free end thereof facing away from the handheld part 4, the catheter tube 3 ends in a catheter tip 1. In this example, this catheter tip 1 has a relatively long embodiment, as is identifiable in FIG. 1. Therefore, the catheter tip 1 preferably has one or more flexible regions 160, at which it can be bent. As a result of this, the catheter tip 1 can also be guided around tight bends through body channels of the patient.

Figure 2:
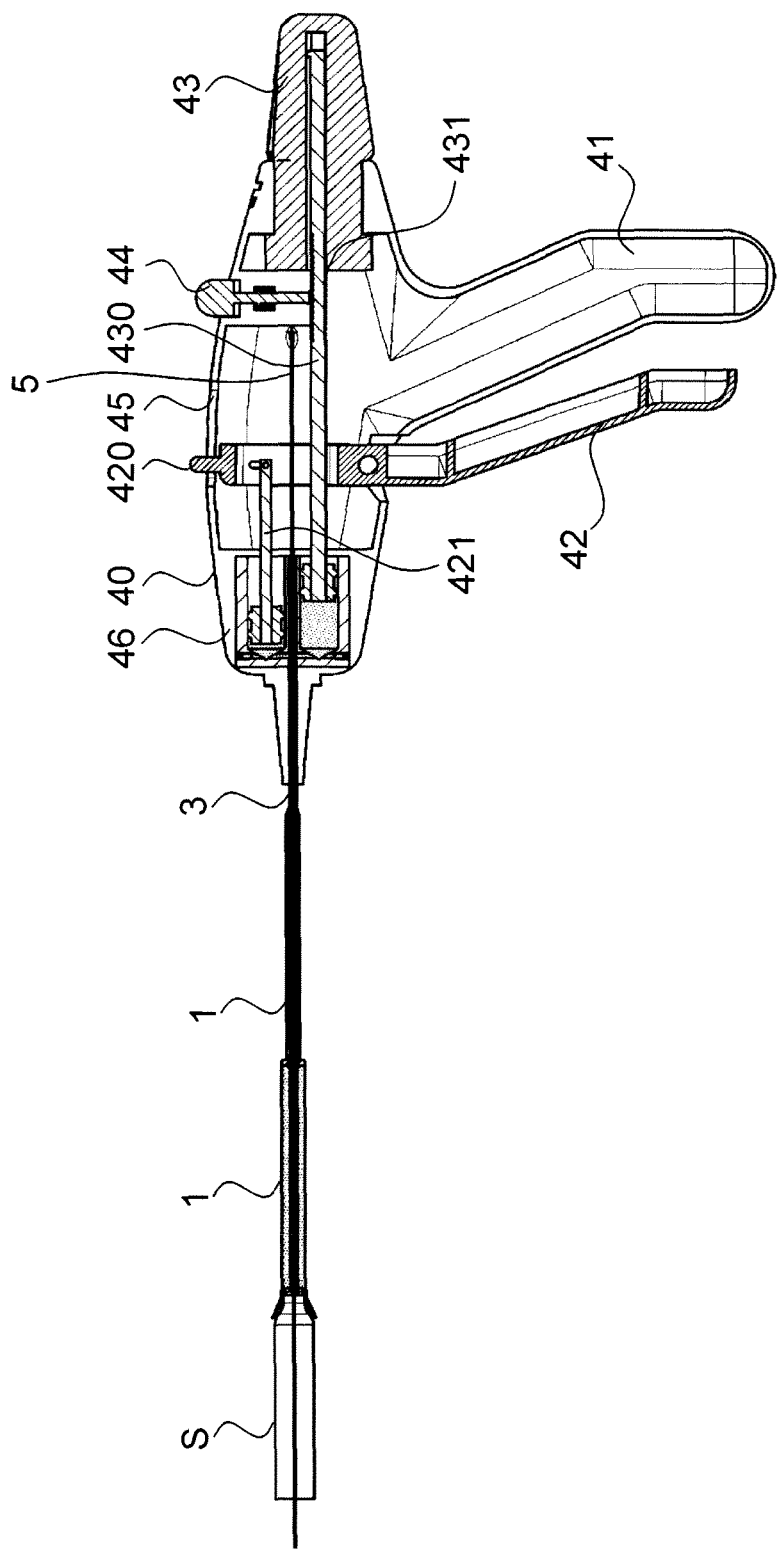
FIG. 2 shows a longitudinal section through the stent applicator in accordance with FIG. 1 with a partly released stent.

A stent S which can be released by means of the handheld part 4 is arranged in the catheter tip 1. In FIG. 1, the stent S is completely held within the catheter tip 1 and therefore not visible. In FIG. 2, it is practically completely released, wherein it is still held in the catheter tip 1 with the back end thereof facing the handheld part 4.

Here, the stent S is depicted schematically. Preferably, this is a self-expanding stent S. It can have any form. By way of example, it can consist of a flexible tube-shaped mesh. Various other forms are known from the prior art. By way of example, the stent can also be provided with a graft, wherein the graft may have flaps or no flaps.

The stent is preferably held in the catheter tip, for example by virtue of being detachably hung in hooks (which are not depicted in this exemplary embodiment). Other types of retention means can also be used.

As is identifiable in FIG. 2, the actuation lever 42 acts on a first plunger rod 421. This plunger rod 421 is part of a hydraulic apparatus 46, which is arranged in the handheld part 4. A protruding lug is embodied at the upper end of the actuation lever 42, which lug penetrates the housing of the main body 40 to the outside and moves as a display pin 420 along a display slit 45 depending on the movement of the actuation lever 42. As a result, as is identifiable in FIG. 1, the current function of the handheld part 4 can be read from the outside.

The rear end of the handheld part 4 is provided with a rotary knob 43. This rotary knob 43 turns a second plunger rod 430 of the hydraulic apparatus 46. This second plunger rod 430 is provided with a thread 431 or it is embodied over a portion as a circumferential toothed rack. A pickup 44 acts on this portion, which pickup engages into the thread 431 or the toothed rack and thus displaces the plunger rod forward in the direction of the catheter tip 1.

Figure 3:
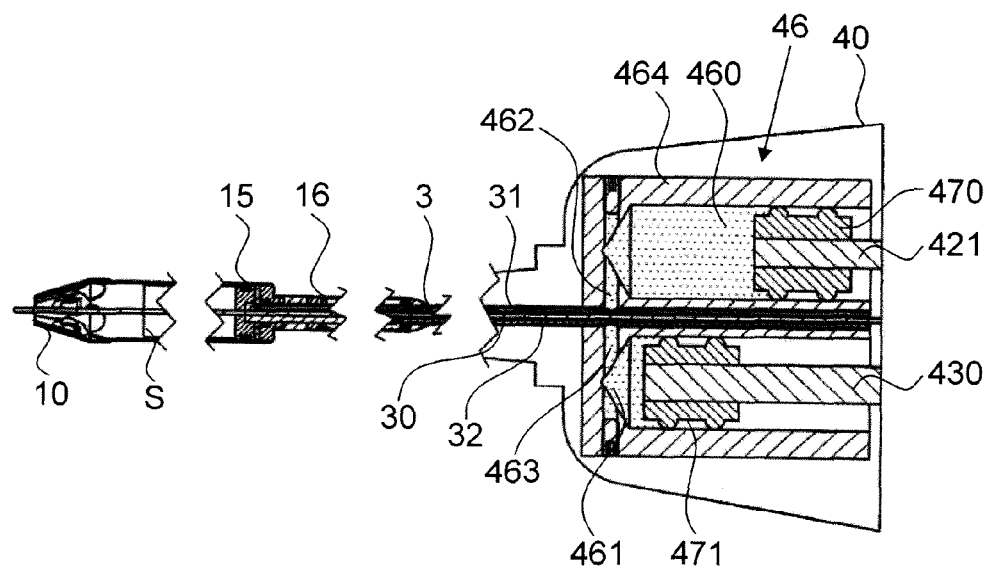
FIG. 3 shows a longitudinal section through individual regions of the stent applicator in accordance with FIG. 1 with a sheathed stent.

As is easily identifiable in FIG. 3, the hydraulic apparatus 46 has a first and a second fluid chamber 460, 461, which are arranged next to one another. The first plunger rod 421 ends in the first fluid chamber 460 with a first plunger 470; the second plunger rod 430 ends in the second fluid chamber 461 with a second plunger 471. In the respective fluid chamber 460, 461, both plungers 470, 471 are displaceable in the longitudinal direction by means of the associated plunger rod 421, 430, wherein they are mounted in a sealing manner in relation to an outer housing 464 of the hydraulic apparatus 46.

In the housing 464 of the hydraulic apparatus 46, a first fluid channel 462 leads from the first fluid chamber 460 to a first entrance opening of a first fluid delivery lumen 31 of the catheter tube 3. A second fluid channel 463 leads from the second fluid chamber 461 to a first entrance opening of a second fluid delivery lumen 32 of the catheter tube 3.

The catheter tube 3 furthermore has a central lumen 30, through which a guide wire 5 can be guided from the handheld part 4 to the catheter tip 1 and therebeyond. As is identifiable in FIG. 1, the proximal end of the guide wire is guided out of the handheld part 4 such that it can be held manually by the user.

Figure 5:
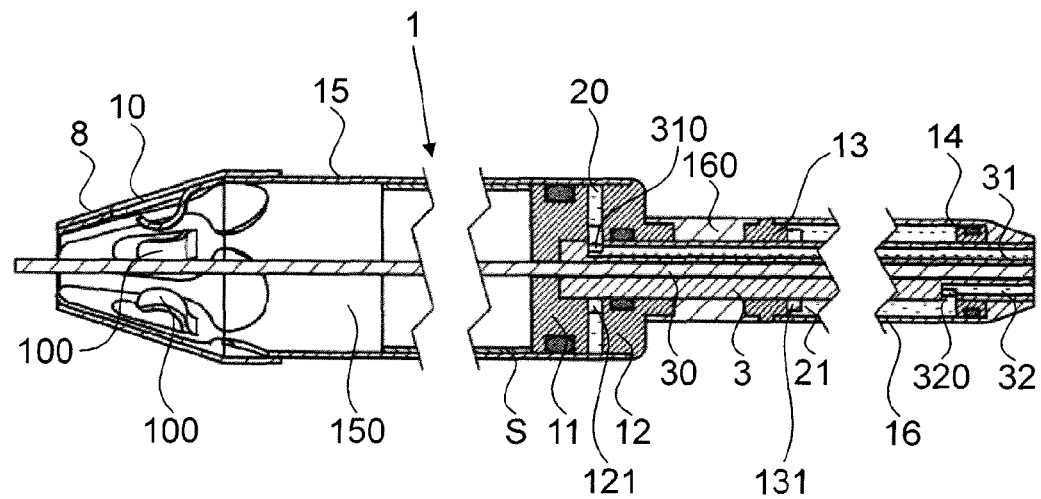
FIG. 5 shows a magnified illustration of the front region in accordance with FIG. 3.

The catheter tip 1 is easily identifiable in FIG. 5. It has two sleeves 15, 16 arranged in succession, which preferably have different external diameters. The two sleeves 15, 16 preferably have a non-elastic but flexible embodiment. They preferably consist of a fiber-reinforced plastic, e.g. reinforced Pebax. The first sleeve 15 forms a stent chamber 150 for receiving the stent S. The internal diameter of the first sleeve 15 is dimensioned in such a way that the stent S can be held in the stent chamber 150 in the radially compressed state.

The front end of the first sleeve 15 facing away from the handheld part 4 merges into spring leaves 10. They form a head part of the catheter. They are preferably embodied integrally with the first sleeve 15. These spring leaves 10 close the front free end of the first sleeve 15 in a petaloid manner. Each spring leaf 10 preferably has an inwardly directed protrusion 100.

The first sleeve 15 is connected in a sealed and secured manner to the second sleeve 16 by way of a first sleeve base 12. The second sleeve 16 preferably has a smaller external diameter than the first sleeve 15. A second sleeve base 13 is arranged in a secure position inside the second sleeve 16, preferably in the central region thereof as seen in the longitudinal direction. This second sleeve base 13 subdivides the inner space of the second sleeve into two chambers. This sleeve base 13 preferably penetrates the wall of the second sleeve 16.

The second sleeve base 13 is arranged at a distance from the first sleeve base 12. The region lying therebetween is embodied as a flexible region 160. It is preferably manufactured from an elastic material, for example silicone.

The first and second sleeve base 12, 13 can also directly adjoin one another or be formed by a common, in particular integral, component. They preferably have a flexible embodiment in these variants such that they can themselves form the hinge or the flexible region 160.

The catheter tube 3 penetrates the second sleeve 16 and ends in the first sleeve 15. A first catheter plunger is arranged securely at the free end thereof. The first catheter plunger 11 is situated in the interior of the first sleeve 15 and forms a handheld part-side wall of the stent chamber 150. The first catheter plunger 11 is held in the first sleeve 15 in a manner displaceable thereto. Here, it is sealed with a first sealing ring 110 in relation to the inner wall of the first sleeve 15.

The space between the first catheter plunger 11 and the first sleeve base 12, the size of which is changeable, forms a first pressure chamber 20, the functionality of which will be explained below. The first fluid lumen 31 of the catheter tube 3 ends in this first pressure chamber 20. The lumen opening leading into this first pressure chamber 20 is provided with the reference sign 310. As a result, a line connection is provided from the first fluid chamber 460 in the handheld piece 4 to the first pressure chamber 20 via the catheter tube 3. This system is filled with a first fluid, preferably a liquid. In particular, a saline solution, a contrast agent or other biocompatible liquids are suitable as a liquid. The liquid is preferably highly viscous in order to ensure the tightness of the system.

Furthermore, a second catheter plunger 14 is securely arranged on the catheter tube 3. It is held displaceably in the longitudinal direction within the second sleeve 16, with it also being sealed in relation to the inner wall of the second sleeve 16 by way of at least one second sealing ring 140. A second pressure chamber 21 is formed between this second catheter plunger 14 and the second sleeve base 13. The second fluid lumen 32 of the catheter tube ends in a second lumen opening 320, which leads into this second pressure chamber 21. Therefore, a line is formed between the second fluid chamber 461 in the handheld part 4 and the second pressure chamber 21 by way of the catheter tube 3. This system is likewise filled with a second fluid, preferably a liquid, in particular a highly viscous liquid. The same examples can be provided as above. Both systems are preferably filled with the same type of fluid. However, the fluids of the two systems do not mix with one another.

The catheter tube 3 penetrates the first and the second sleeve base 12, 13 and is displaceable in the longitudinal direction relative to these. The first sleeve base 12 is sealed in relation to the outer jacket of the catheter tube 3 by way of a sealing ring 120.

The more precise mode of action of the hydraulic apparatus 46 with the double action cylinder is identifiable in the overview of FIGS. 3 to 6. In FIGS. 3 and 5, the stent S is arranged in the catheter tip and completely sheathed. The first plunger 470 is situated in the retracted position and the display pin 421 visible in FIG. 2 is situated at the rear location, i.e. different to what is depicted in FIG. 2. The first fluid chamber 460, which is formed by the first cylinder, is filled with the first fluid. The volume of the first pressure chamber 20 is reduced to a minimum. The first sleeve base 12 is preferably drawn near to the first catheter plunger 11 as far as a spacer 121 in the first pressure chamber 20.

In this position, the second piston 471 is situated at the front, catheter-side stop of the second fluid chamber 461. The second fluid is predominantly in the second pressure chamber 21. The latter is preferably extended to the maximum thereof, i.e. the second catheter piston 14 is situated at the handheld part-side end of the second sleeve 16 at the maximum distance from the second sleeve base 13.

This situation is referred to as "loaded". The actuation lever 42 of the handheld part 4 is not actuated.

Figure 4:
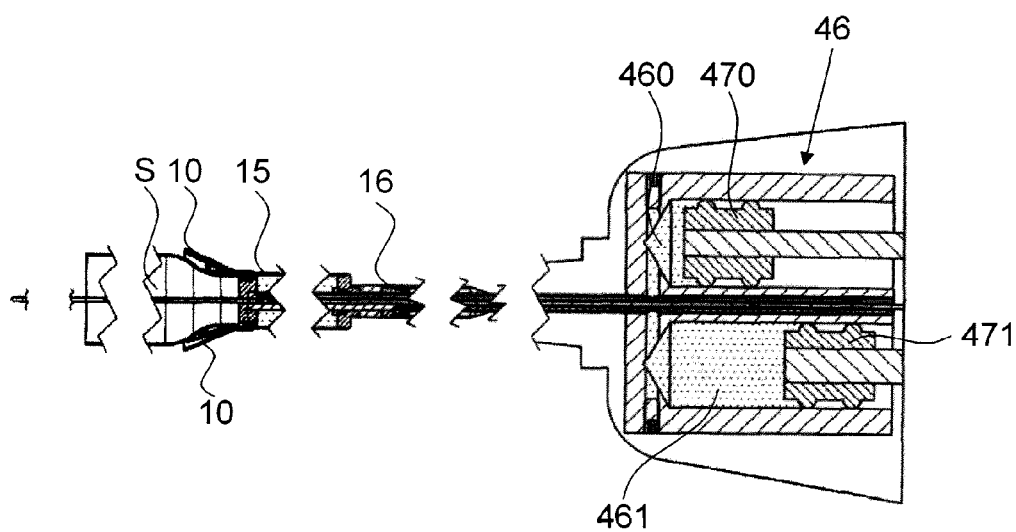
FIG. 4 shows a longitudinal section through individual regions of the stent applicator in accordance with FIG. 1 with a partly released stent.
Figure 6:
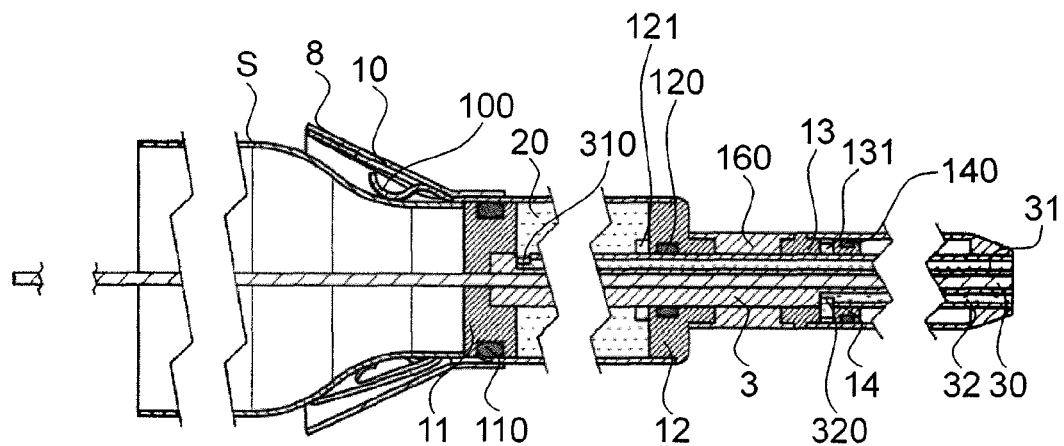
FIG. 6 shows a magnified illustration of the front region in accordance with FIG. 4.

If the actuation lever 42 now is actuated, i.e. pulled toward the handle 41, the first plunger rod 421 pushes the first plunger 470 in the forward direction in the cylinder and the first fluid is guided into the first pressure chamber 20. The display pin 420 is pushed forward together with the first actuation rod 421 and now shows, as depicted in FIG. 2, the "released" situation of the stent S. This situation is depicted in FIGS. 4 and 6. The first sleeve base 12 arranged in a displaceable manner around the catheter tube 3 is pushed backward in the direction of the handheld part 4 and pulls or pushes the first and second sleeve 15, 16 backward.

Since the stent S rests on the first catheter plunger 11, the spring leaves 10 impact on the latter and open outwardly. They then slide over the stent S such that the latter is released. The released region of the stent S thereupon unfolds, preferably independently, the material of the stent S relaxes and the stent S affixes itself in the anatomical structure of the region of use, preferably by residual compression or residual pretension.

The second sleeve 16 slides over the second catheter plunger 14 and the second sleeve base 13 thus approaches said plunger 14 up to a spacer 131. As a result, the volume in the second pressure chamber 21 is reduced and the second fluid is pressed back into the second fluid chamber 461 in the handheld part 4. The second piston 471 is moved backward. To this end, the pickup 44 in the handheld part 4 is at a distance from the second actuation rod 430, i.e. it is slightly pulled out of the main body 40 and therefore releases the toothed rack 431.

If the released or partly released stent S should now be retracted again into the catheter tip 1 and be repositioned or completely removed from the body of the patient, this is implemented by means of the rotary knob 43 of the handheld part 4. To this end, the pickup 44 engages with the thread 431 of the second actuation rod 430. If the rotary knob 43 is rotated manually, the second actuation rod 430 is displaced forwardly. The second piston 471 presses again the second fluid back into the second pressure chamber 21 of the catheter tip 1 and the two sleeves 15, 16 are pushed forward again. The spring leaves 10 slide over the stent and recapture the latter. If necessary, they open up for this purpose.

Here, the first fluid is, in turn, guided back from the first pressure chamber 20 into the first fluid chamber 460 until the "loaded" situation in accordance with FIGS. 3 and 5 has once again been reached. As soon as the stent S is largely or completely re-sheathed, the position within the body of the patient can be corrected as desired and the stent S can subsequently be released again.

Since high compressive forces are required for this re-sheathing of the stent S, a flower-like structure, in this case the spring leaves 10, was developed for reducing the forces. There are preferably two, three, four, five or more spring leaves 10. They preferably have a flexible embodiment relative to the first sleeve and automatically assume their closed position in accordance with FIGS. 3 and 5. They preferably consist of nitinol. During opening, a funnel is generated, like in the case of an opening flower. This funnel eases the sliding out, but also the re-sheathing as the stent is not pressed back into its compressed form over a sharp edge but via this funnel geometry.

When the stent S is placed correctly, the delivery system can be pulled out of the patient body. Here, the spring leaves 10 at the catheter tip 1 reduce the risk of traumatization. Since they automatically spring back into their closed position after the stent S is released, they do not form an increased resistance when pulling out the system.

The closed petaloid structure formed by the spring leaves 10 is preferably coated by an elastic protection tube 8. The protection tube is preferably manufactured from silicone. This protection tube 8 has an open embodiment in the proximal and distal direction and is preferably adhesively bonded at the proximal end. A shrinking tube can also be used as protection tube 8. The protection tube 8 completely surrounds the spring leaves 10. When the spring leaves 10 are opening, said protection tube can be stretched enough to allow the stent S to be released. Moreover, it is sufficiently elastic to likewise retract during the renewed closing of the spring leaves 10 and thus securely surround these again, at least in an approximate manner.

Arranging the pressure chambers 20, 21 of the catheter tip in succession in the longitudinal direction is advantageous in that the catheter tip or the catheter head can have a relatively small external diameter. The size of the stent S and the wall strength of the sleeve define this external diameter.

Variations of this embodiment are possible. Thus, a single sleeve or multipiece sleeve, which is preferably flexible and in which the two plungers and the two bases or the one base are arranged, can be used instead of two sleeves 15, 16, for example.

FIGS. 7 to 15 depict a second embodiment of the delivery system according to the invention. In contrast to the first exemplary embodiment, the two pressure chambers are now arranged concentrically with one another. This is advantageous in that the catheter tip can have a shorter embodiment and therefore can be passed more easily about tight bends in the body channels.

The delivery system has a catheter tip 1 with an external sleeve 17. This catheter tip 1, more precisely the outer sleeve 17, can be closed off at the front, distal end by a catheter head 7. The outer sleeve 17 preferably has a non-elastic but flexible embodiment. It is preferably made of fiber-reinforced plastic, e.g. reinforced Pebax.

Figure 7:
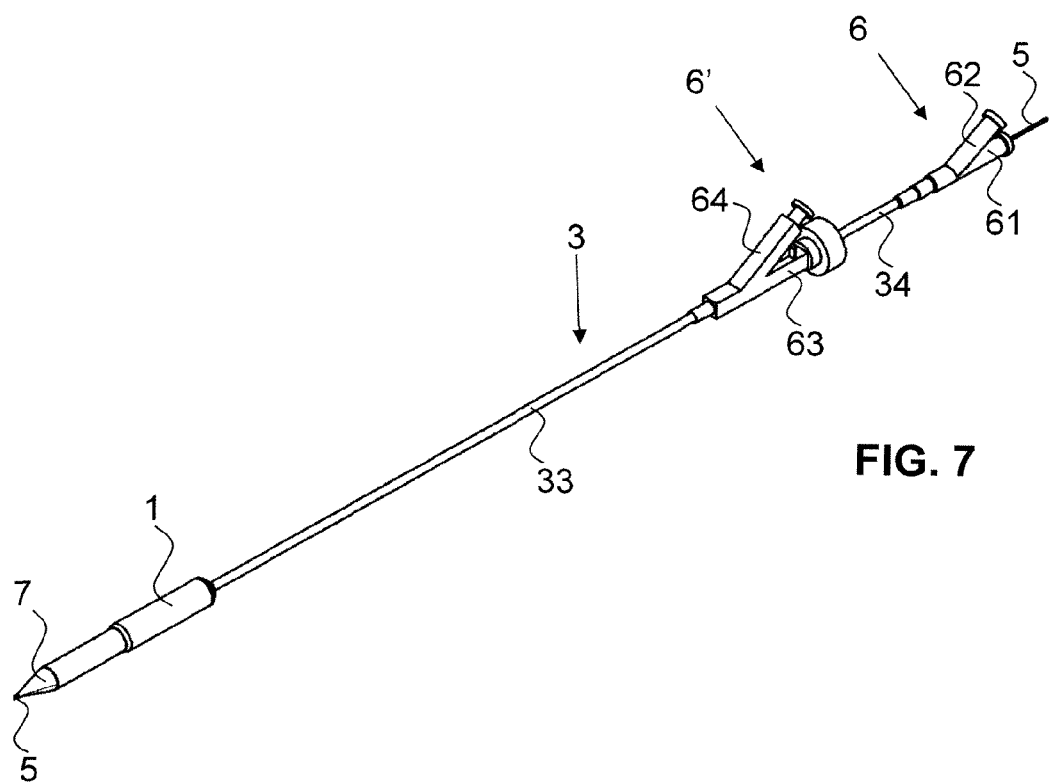
FIG. 7 shows a perspective illustration of a stent applicator according to the invention in a second embodiment.

As is identifiable in FIG. 7, a flexible catheter tube 3, preferably made of Pebax, is securely connected to the catheter tip 1. At the rear, i.e. proximal, end thereof, the catheter tube is connected to a connector unit, preferably to two Y-connectors 6, 6' arranged in succession. A guide wire 5 passes through the connector unit 6, 6', the catheter tube 3, the catheter tip 1 and the catheter head 7, wherein said guide wire protrudes from a first connection part 61 of the connector unit, more precisely from the first Y-connector 6. The guide wire 5 usually serves to insert the catheter tube 3 into a body channel of the patient.

A second connection part 62 of the first Y-connector 6 serves to introduce a fluid into an inner tube portion 34 of a catheter tube 3 up to the catheter tip 1. This is for example implemented by a manually or motor-driven syringe. Suitable fluids have already been specified above.

The inner tube portion 34 passes through the second Y-connector 6', more precisely a third connection part 63 of same, and is held therein in a manner displaceable in the longitudinal direction. A fourth connection part of the second Y-connector 6' serves to bring a second fluid through an outer tube portion 33 of the catheter tube 3 up to the catheter tip 1. In this example, the second fluid also extends completely separately from the first fluid. However, it preferably consists of the same substance.

Figure 8:
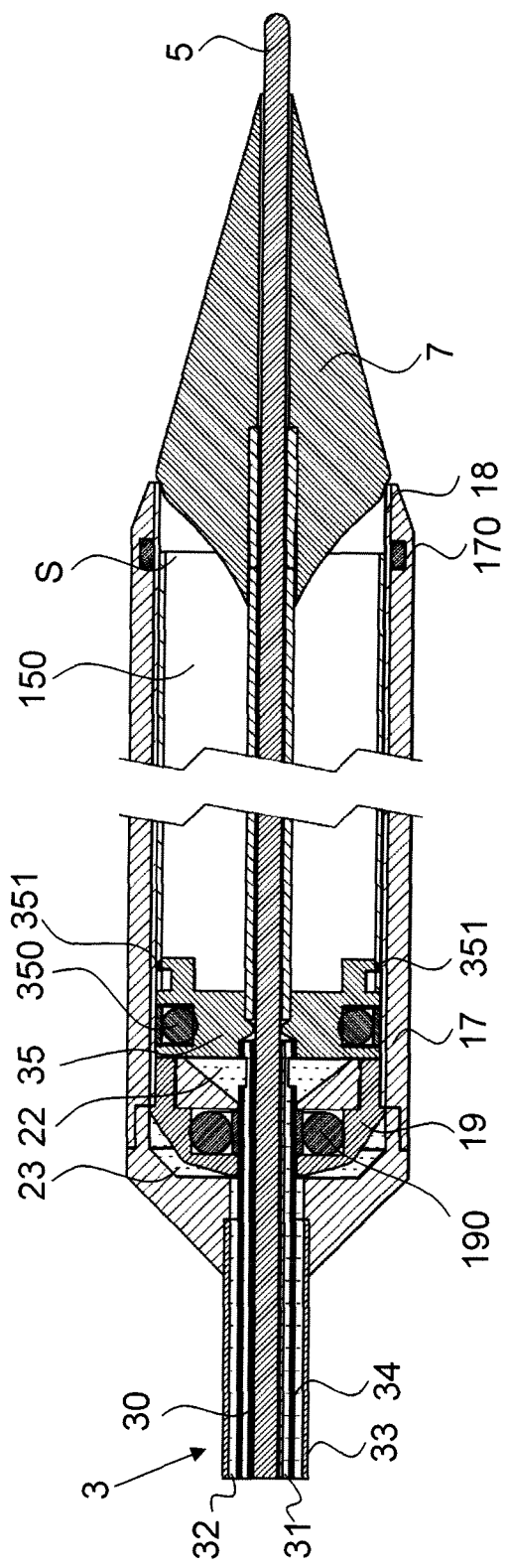
FIG. 8 shows a longitudinal section through a front region of the stent applicator with a sheathed stent in accordance with FIG. 7.

FIG. 8 shows a longitudinal section through the distal region of the delivery system. In this case, the catheter tube 3 is also a multi-lumen flexible tube. It has an outer tube portion 33 and an inner tube portion 34. The inner tube portion 34 is displaceable in the longitudinal direction relative to the outer tube portion 33.

The catheter tube 3 has a central lumen 30 for receiving the guide wire 5, which is displaceable in the longitudinal direction relative thereto. Furthermore, the tube 3 once again has two fluid lumens 31, 32, which in this case are arranged concentrically around the central lumen 30. The first, inner fluid lumen 31 is situated in the inner tube portion 34. The second, outer fluid lumen 32 is formed by the cavity between outer and inner tube portion 33, 34.

The outer jacket of the catheter tip 1 is formed by the outer sleeve 17. At the rear, proximal end of the outer sleeve 17, the outer tube portion 33 of the catheter tube 3 is securely connected to this outer sleeve 17. At this end, the outer sleeve 17 is otherwise embodied in a closed manner. The second fluid lumen 32 ends in a rear, proximal cavity of the outer sleeve 17 which forms a second pressure chamber 23.

An inner sleeve 18 is held in the outer sleeve 17 in a manner displaceable in the longitudinal direction. Said inner sleeve is sealed in relation to the outer sleeve by one or more sealing rings 170. At the rear proximal end thereof, it is closed by a sleeve base 19 which is securely connected thereto. This sleeve base 19 is penetrated by the inner tube portion 34 of the catheter tube 3. In the longitudinal direction, it is displaceable relative to the inner tube portion 34, wherein it is sealed in relation to the inner tube portion 34 by a sealing ring 190.

Distally from this sleeve base 19, the inner tube portion 34 penetrates a catheter plunger 35 which is securely connected to the inner tube portion 34 and displaceable in the longitudinal direction relative to the inner, and therefore also to the outer, sleeve 18, 17. This catheter plunger 35 is sealed in relation to the inner sleeve 18 by a sealing ring 350. It is also possible, as is depicted here, for there to be a plurality of sealing rings, in particular two sealing rings 350. The plunger 35 can have an integral or multi-part embodiment.

A first pressure chamber 22 is formed between the sleeve base 19 and the catheter plunger 35. The first fluid lumen 31 ends in this first pressure chamber 22.

A stent chamber 150 for receiving the stent S is formed distally from the catheter plunger 35 in the inner sleeve 18. In this case, the stent S is also only depicted schematically. It can have the conventional embodiments known from the prior art.

The distal end of the catheter plunger 35 forms a proximal rear wall of the stent chamber 150. The distal wall is formed by the catheter head 7, which is securely connected to the catheter tube 3 and displaceable together with the latter. The catheter head 7 is dimensioned in such a way that it closes the distal end of the inner sleeve 18.

The mode of action of this delivery system is identifiable in FIGS. 9 to 15.

Figure 9:
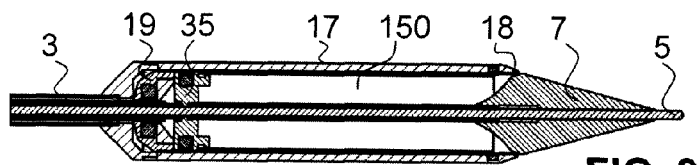
FIG. 9 shows a longitudinal section through a front region of the stent applicator in accordance with FIG. 7 with a completely sheathed stent.

In FIG. 9, the stent S is loaded in the stent chamber 150, wherein the catheter tip 1 is closed by the catheter head 7.

Figure 10:
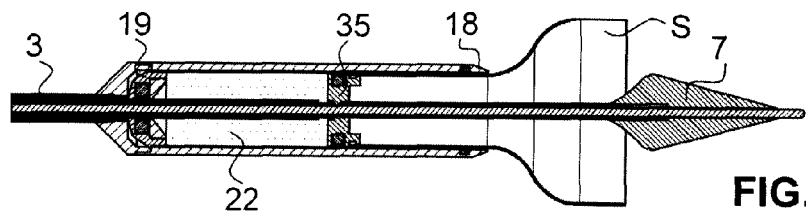
FIG. 10 shows the stent applicator in accordance with FIG. 9 with a partly released stent.

In FIG. 10, the first fluid is now introduced into the first pressure chamber 22 by the first fluid lumen 31. As a result, the outer and inner sleeve 17, 18 move backward, i.e. in the proximal direction, together with the outer tube portion 33. The distal access to the inner sleeve 18 and also the stent S are released. The stent S can unfold.

Figure 11:
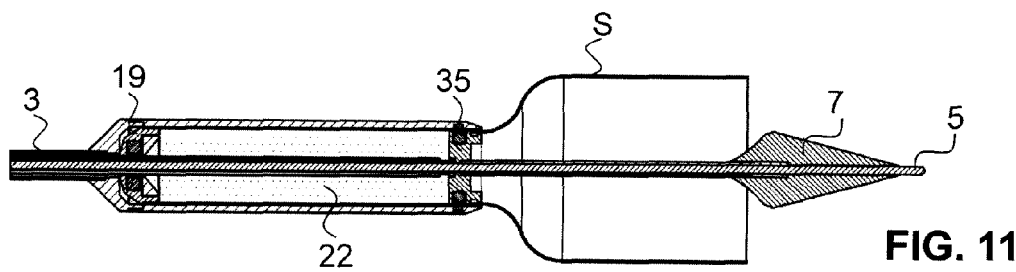
FIG. 11 shows the stent applicator in accordance with FIG. 9 with a stent in an advanced state of release.

FIG. 11 depicts the state in which the front end of the sleeves 17, 18 have reached the catheter plunger 35 and therefore the first pressure chamber 22 has a maximum extent. The stent S is practically exposed, but it is still held by the retention means, in this case hooks 351, of the piston 35.

Figure 12:
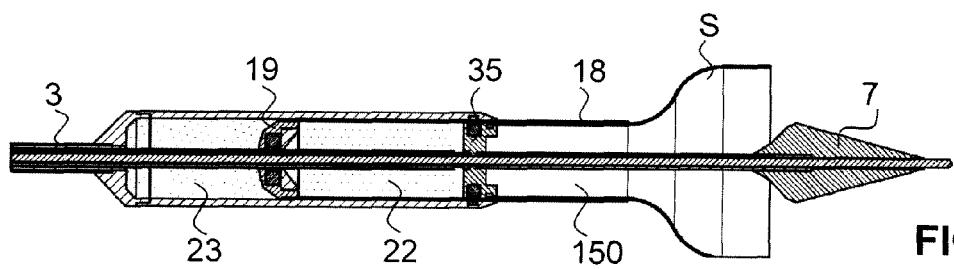
FIG. 12 shows the stent applicator in accordance with FIG. 9 with a partly re-sheathed stent.

If the stent S should now be repositioned in situ or even completely re-sheathed, the second fluid is now introduced into the second pressure chamber 23 by the second fluid lumen 32. The latter extends towards the distal end and pushes the sleeve base 19 toward the distal end together with the inner sleeve 18 and therefore out of the outer sleeve 17. This is depicted in FIG. 12. The inner sleeve 18 slides over the stent S and recaptures the latter.

Figure 13:
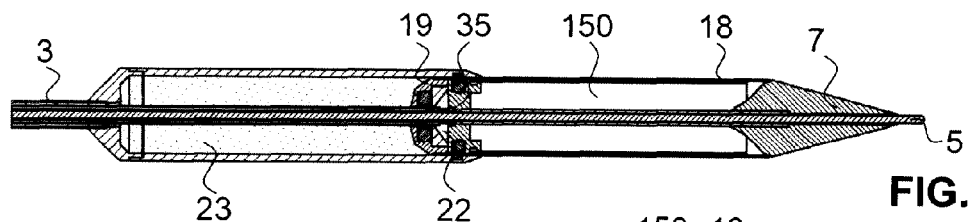
FIG. 13 shows the stent applicator in accordance with FIG. 9 with a stent in an advanced state of sheathing, analogous to FIG. 7.

In FIG. 13, the sleeve base 19 has reached the plunger 35, i.e. the second pressure chamber 23 has the maximum extent. The first fluid was once again pressed out of the first pressure chamber 22. The first pressure chamber 22 has once again reached minimum size. The first fluid can also be actively removed from the first pressure chamber 22. The inner sleeve 18 has again completely shifted over the stent S and the catheter head 7 closes the inner sleeve 18.

Figure 14:
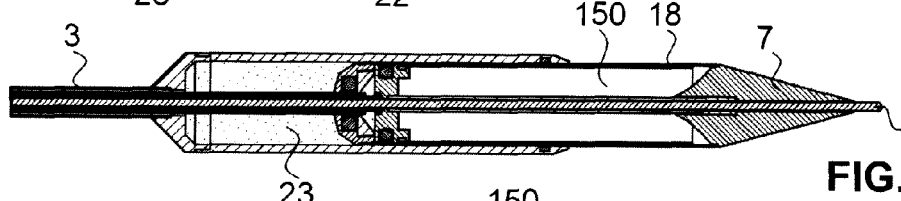
FIG. 14 shows the stent applicator in accordance with FIG. 9 when re-sheathing the inner sleeve and FIG. 15 shows the stent applicator in accordance with FIG. 9 in the new initial position thereof.

In accordance with FIG. 14, the inner sleeve 18 can now, together with the stent S, be re-sheathed by the outer sleeve 17 by virtue of the second fluid being removed from the second pressure chamber 23. The removal of the fluid is preferably once again implemented manually or by way of motor-driven syringes or pumps.

Figure 15:
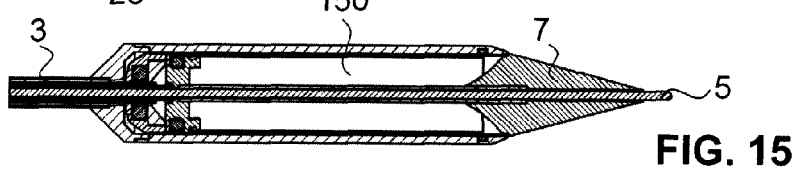

The situation in accordance with FIG. 15 corresponds to that in accordance with FIG. 9, i.e. the catheter tip is loaded again, i.e. the stent is sheathed, and the pressure chambers are more or less empty and minimized in terms of volume.

Variations of this embodiment are possible. Thus, for example, the spring leaves and, preferably, also the protection tube in accordance with the first example can be arranged at the inner sleeve instead of the conventional catheter head in accordance with FIGS. 7 to 15. Moreover, a similar handheld part in accordance with the first exemplary embodiment can also be used in place of the Y-connector.

Thanks to the delivery system according to the invention, a stent can be released at a well-defined point, but also be re-sheathed relatively atraumatically and repositioned in situ.

LIST OF REFERENCE SIGNS

| | |
|---|---|
| 1 | Sleeve |
| 10 | Spring leaf |
| 100 | Protrusion |
| 11 | First catheter plunger |
| 110 | First sealing ring |
| 12 | First sleeve base |
| 120 | Second sealing ring |
| 121 | Spacer |
| 13 | Second sleeve base |
| 131 | Spacer |
| 14 | Second catheter plunger |
| 140 | Third sealing ring |
| 15 | First sleeve |
| 150 | Stent chamber |
| 16 | Second sleeve |
| 160 | Flexible region |
| 17 | Outer sleeve |
| 170 | Sealing ring |
| 18 | Inner sleeve |
| 19 | Sealing ring |
| 190 | Sealing ring |
| 20 | First pressure chamber |
| 21 | Second pressure chamber |
| 22 | First pressure chamber |
| 23 | Second pressure chamber |
| 3 | Catheter |
| 30 | Central lumen |
| 31 | First fluid lumen |
| 310 | First lumen opening |
| 32 | Second fluid lumen |

-continued

LIST OF REFERENCE SIGNS

| | |
|---|---|
| 320 | Second lumen opening |
| 33 | Outer tube portion |
| 34 | Inner tube portion |
| 35 | Catheter plunger |
| 350 | Sealing ring |
| 351 | Hook |
| 4 | Handheld part |
| 40 | Main body |
| 41 | Handle |
| 42 | Actuation lever |
| 420 | Display pin |
| 421 | First plunger rod |
| 43 | Rotary knob |
| 430 | Second plunger rod |
| 431 | Teeth |
| 44 | Locking device |
| 45 | Display slit |
| 46 | Hydraulic apparatus |
| 460 | First fluid chamber |
| 461 | Second fluid chamber |
| 462 | First fluid channel |
| 463 | Second fluid channel |
| 464 | Housing |
| 470 | First plunger |
| 471 | Second plunger |
| 5 | Guide wire |
| 6 | First Y-connector |
| 6' | Second Y-connector |
| 61 | First connection part |
| 62 | Second connection part |
| 63 | Third connection part |
| 64 | Fourth connection part |
| 7 | Catheter head |
| 8 | Protection tube |
| S | Stent |

The invention claimed is:

1. A delivery system for delivering a stent in a body of a patient, comprising:
a flexible catheter tube with a proximal end and a distal end for delivering the stent to a predetermined point in a body vessel of the patient's body, and
a catheter tip with a longitudinal direction, which is arranged at the distal end of the catheter tube, wherein the catheter tip has a stent chamber for receiving the stent,
wherein the catheter tip has a first pressure chamber,
wherein a first fluid channel extends in the catheter tube from the proximal end to the first pressure chamber of the catheter tip,
wherein a volume of the first pressure chamber is enlargeable by delivering a first fluid from the first fluid channel to the first pressure chamber and, as a result thereof, the stent is releasable from the stent chamber at the predetermined point in the body vessel,
wherein the catheter tip has a second pressure chamber,
wherein a second fluid channel extends in the catheter tube from the proximal end to the second pressure chamber,
wherein a volume of the second pressure chamber is enlargeable by delivering a second fluid from the second fluid channel to the second pressure chamber, as a result of which a partly released stent is retractable into the stent chamber from the predetermined point in the body vessel and wherein the catheter tip has a first sleeve, in which one of the first and the second pressure chamber is arranged, and a second sleeve, in which the other one of the first and the second pressure chamber is arranged.

2. The delivery system as claimed in claim 1, wherein the catheter tube has a guide lumen for passing a guide wire therethrough and wherein the first sleeve and the second sleeve are displaceable relative to the guide lumen, wherein the guide lumen remains unchanged in terms of its location with respect to the predetermined point and the first and the second sleeve move relative to the predetermined point.

3. The delivery system as claimed in claim 1, wherein the first sleeve and the second sleeve are displaceable together relative to the catheter tube in the longitudinal direction.

4. The delivery system as claimed in claim 1, wherein the catheter tip has at least one flexible region such that it is flexible transverse to the longitudinal direction.

5. The delivery system as claimed in claim 1, wherein the second sleeve is arranged within the first sleeve and in a manner displaceable relative to the latter and wherein the first pressure chamber is arranged in the second sleeve and the second pressure chamber is arranged in the first sleeve.

6. The delivery system as claimed in claim 5,
wherein the catheter tube has an outer tube portion and an inner tube portion arranged therein,
wherein the outer tube portion is displaceable in the longitudinal direction relative to the inner tube portion,
wherein the first sleeve is securely connected to the outer tube portion and displaceable in the longitudinal direction in a sealing sliding manner in relation to the inner tube portion,
wherein a catheter plunger is present, which plunger is securely connected to the inner tube portion and displaceable in the longitudinal direction in a sealing manner relative to the second sleeve,
wherein the second sleeve is sealed at the proximal end thereof by a sleeve base, which is securely connected to the former and which is displaceable in the longitudinal direction in a sealing sliding manner relative to the first sleeve,
the first pressure chamber is embodied between the sleeve base and the catheter plunger, and
wherein the second pressure chamber is embodied between a proximal end of the first sleeve and the sleeve base.

7. The delivery system as claimed in claim 6, wherein the catheter plunger forms a proximal end of the stent chamber.

8. The delivery system as claimed in claim 1, wherein the first sleeve and the second sleeve are arranged in succession in the longitudinal direction and wherein, in the longitudinal direction, they are connected to one another in a non-displaceable manner relative to one another.

9. The delivery system as claimed in claim 1,
wherein a first catheter plunger which forms a distal end of the first pressure chamber is arranged at the distal end of the catheter tube,
wherein the first sleeve is displaceable in the longitudinal direction in a sealing sliding manner relative to this first catheter plunger,
wherein the first pressure chamber has a first sleeve base which forms a proximal end of the first pressure chamber,
wherein the first sleeve base is securely connected to the first sleeve and arranged in a sealing sliding manner around the catheter tube,
wherein a second catheter plunger which forms a proximal end of the second pressure chamber is arranged on the catheter tube,
wherein the second sleeve is displaceable in the longitudinal direction in a sealing sliding manner relative to this second catheter plunger,
wherein the second pressure chamber has a second sleeve base which forms a distal end of the second pressure chamber,
wherein the second sleeve base is securely connected to the second sleeve and arranged in a sealing sliding manner around the catheter tube.

10. The delivery system as claimed in claim 1, wherein the catheter tip, at the distal end thereof, has a catheter head in the form of spring leaves, wherein the spring leaves are inclined with respect to one another in a petaloid manner and at least partly close an opening to the stent chamber.

11. The delivery system as claimed in claim 10, wherein each spring leaf has an inwardly directed protrusion.

12. The delivery system as claimed in claim 10, wherein there is an elastic protection tube which surrounds the spring leaves.

13. The delivery system as claimed in claim 1, wherein it furthermore has a manipulation part which is arranged at the proximal end of the catheter tube, wherein, by means of the manipulation part, the stent can be released from, and returned back into, the stent chamber at the predetermined point in the body vessel.

14. The delivery system as claimed in claim 13, wherein the manipulation part has a hydraulic apparatus with a first fluid chamber with a first plunger and a second fluid chamber with a second plunger, wherein a proximal end of the first fluid lumen is connected to the first fluid chamber and a proximal end of the second fluid lumen is connected to the second fluid chamber.

15. The delivery system as claimed in claim 14, wherein the first plunger is actuatable by means of an actuation lever and the second plunger is actuatable by means of a rotary knob.

16. A catheter head of a catheter tip of a delivery system for delivering a stent in a body of a patient, the delivery system comprising:
a flexible catheter tube with a proximal and a distal end for delivering the stent to a predetermined point in a body vessel of the patient's body,
the catheter tip with a longitudinal direction, the catheter tip being arranged at the distal end of the catheter tube,
wherein the catheter tip, at the distal end thereof, has the catheter head and
wherein the catheter tip has a stent chamber for receiving the stent,
wherein the catheter tip has a first pressure chamber,
wherein a first fluid channel extends in the catheter tube from the proximal end to the first pressure chamber of the catheter tip, and
wherein a volume of the first pressure chamber is enlargeable by delivering a first fluid from the first fluid channel to the first pressure chamber and, as a result thereof, the stent is releasable from the stent chamber at the predetermined point in the body vessel,
wherein the catheter tip has a second pressure chamber,
wherein a second fluid channel wherein extends in the catheter tube from the proximal end to the second pressure chamber,
wherein a volume of the second pressure chamber is enlargeable by delivering a second fluid from the second fluid channel to the second pressure chamber, as a result of which a partly released stent is retractable into the stent chamber from the predetermined point in the body vessel and wherein the catheter tip has a first sleeve, in which one of the first and second pressure chamber is arranged, and a second sleeve, in which the other one of the first and second pressure chamber is arranged, wherein the catheter head has spring leaves which are inclined with respect to one another in a petaloid manner and which open from the inside to the outside by pressure.

\* \* \* \* \*